(12) United States Patent
Haselwood

(10) Patent No.: US 11,690,603 B2
(45) Date of Patent: Jul. 4, 2023

(54) BIOPSY TRAY AND METHOD OF OBTAINING A BIOPSY SPECIMEN

(71) Applicant: Shanon Haselwood, Peachtree City, GA (US)

(72) Inventor: Shanon Haselwood, Peachtree City, GA (US)

( * ) Notice: Subject to any disclaimer, the term of this patent is extended or adjusted under 35 U.S.C. 154(b) by 1026 days.

(21) Appl. No.: 16/444,710

(22) Filed: Jun. 18, 2019

(65) Prior Publication Data

US 2020/0397417 A1 Dec. 24, 2020

(51) Int. Cl.
| | | |
|---|---|---|
| *A61B 10/00* | (2006.01) | |
| *A61B 10/06* | (2006.01) | |
| *A61B 50/33* | (2016.01) | |
| *A61B 50/30* | (2016.01) | |
| *A61B 50/00* | (2016.01) | |
| *A61B 50/39* | (2016.01) | |
| *A61L 2/00* | (2006.01) | |

(52) U.S. Cl.
CPC .......... *A61B 10/0096* (2013.01); *A61B 10/06* (2013.01); *A61B 50/33* (2016.02); *A61B 50/39* (2016.02); *A61B 2050/005* (2016.02); *A61B 2050/3008* (2016.02); *A61L 2/0005* (2013.01)

(58) Field of Classification Search
CPC .......... A61B 10/0096; A61B 2050/005; A61B 2050/3008; A61B 90/70; A61N 50/33; A61N 50/39; A61L 2/005; A61L 2202/10; A61L 2202/23; A61L 2202/24
See application file for complete search history.

(56) References Cited

U.S. PATENT DOCUMENTS

| | | | | |
|---|---|---|---|---|
| 3,244,125 | A * | 4/1966 | Mackey ................. | A47B 31/06 |
| | | | | D12/419 |
| 4,948,564 | A * | 8/1990 | Root ......................... | B01L 9/06 |
| | | | | 422/534 |
| 5,609,826 | A * | 3/1997 | Cargill ................. | B01J 19/0046 |
| | | | | 422/570 |
| 2008/0045860 | A1* | 2/2008 | Miller .................... | A61B 46/10 |
| | | | | 600/567 |
| 2009/0287113 | A1* | 11/2009 | Freeman ................. | A61B 10/06 |
| | | | | 600/564 |
| 2009/0291449 | A1* | 11/2009 | Knapp, Jr. .......... | A61B 10/0096 |
| | | | | 435/6.12 |
| 2011/0226766 | A1* | 9/2011 | Baker .................... | A61B 50/33 |
| | | | | 220/23.88 |
| 2017/0056122 | A1* | 3/2017 | Ramsey ................. | A61B 90/94 |

* cited by examiner

*Primary Examiner* — David J. McCrosky
*Assistant Examiner* — Nidhi N Patel
(74) *Attorney, Agent, or Firm* — R. William Graham

(57) ABSTRACT

An improved biopsy tray includes a container having bottom surface and continuous perimeter wall extending upward therefrom to form a cleaning zone which is sufficient to hold an adequate amount of fluid for cleaning a biopsy forceps, and at least one specimen bottle receiving receptacle adjacent the perimeter wall to receive and retain a specimen bottle. A method of obtaining a biopsy specimen includes employing the tray of the invention.

3 Claims, 6 Drawing Sheets

BIOPSY TRAY AND METHOD OF OBTAINING A BIOPSY SPECIMEN

BACKGROUND OF THE INVENTION

1. Field of the Invention

The present invention relates to a biopsy tray, biopsy kits, and methods of processing tissue specimens.

2. Description of the Related Art

Biopsy forceps are flexible with movable cup-shaped jaws, used to obtain biopsy specimens by introduction through a specially designed endoscope. Specimens can be collected using these forceps and once the tissue sample has been obtained within the forceps, the physician, nurse or attendant needs to transfer the specimen to the pathology lab in an effective and efficient manner.

Currently, the specimen is obtained and a first attendant will obtain and handle a specimen bottle opening the cap while a second attendant inserts the specimen into the bottle and the first attendant replaces the cap to make this transition of the specimen to the pathologist. However, this is often a tedious task as care must be taken to not have the forceps with specimen touch or worse yet nick the attendant handling the specimen bottle. If this happens, two problems occur in which there is a failure to securely transition the sample to the pathologist but more importantly the attendant has to undergo testing to assure no potential health threat occurred to the attendant.

In view of the difficulty in transferring tissue specimens during a biopsy to a pathology lab using current techniques, there is a need for an improved device and technique for handling, processing, and transferring fresh tissue specimens as well as reduced the risk to the attendants handling such specimens.

SUMMARY OF THE INVENTION

It is an object to improve the devices used in obtaining biopsy specimens.

It is another object to improve the method used in obtaining biopsy specimens.

It is further object to provide an improved biopsy tray.

Accordingly, one aspect of the invention is directed to an improved biopsy tray. The tray is preferably made of a disposable and recyclable sterile plastic which includes a bottom surface and continuous perimeter wall extending upward therefrom to form a container sufficient to hold an adequate amount of fluid for cleaning (e.g., 250 ml water)—referred to hereinafter as a "cleaning zone." Additionally the perimeter wall includes at least one and preferably a plurality of formed specimen bottle receiving receptacle(s) to receive and retain a standard formalin specimen bottle (e.g., 20 ml). One embodiment of the invention provides for the perimeter wall to have four sides with a formed specimen bottle receiving receptacle in a corner between each of the walls. The specimen bottles would be disposed in the specimen bottle receiving receptacles post water being placed in the cleaning zone of the tray, which aids in the stability of handling the same during the procedure. Preferably, the specimen bottle receiving receptacles are formed as part of the tray to isolate them from the cleaning zone. Once water is placed in the tray cleaning zone and the specimen bottles are inserted into the bottle receiving receptacles, the lids of the bottles are removed and are ready to receive the specimen from the forceps. By so providing, it is not necessary that an attendant handle the specimen bottle near the forceps thus minimizing contamination or health risk. Preferably, the tray is configured to at least slightly nest on top of a like formed tray thus providing for ease of storage.

Another aspect of the invention is to provide a kit which includes the above tray, a biopsy forceps and a biopsy cover for performing a biopsy. Yet another aspect includes a method of obtaining a biopsy specimen. The method includes providing a tray of the type described above, filling the tray with a sufficient amount of cleaning fluid (water) to enable cleaning of a biopsy forceps post procedure, placing one or more specimen bottle in one or more specimen bottle receiving receptacle and removing a cap from each one or more specimen bottle. The method further includes employing a biopsy forceps to remove a tissue specimen from a patient and place the specimen into one of the specimen bottles and removing the forceps from the tray area. The method provides for securing the cap to the specimen bottle and removing the specimen bottle from the tray. Finally, the method can include repeating the last step using the biopsy forceps to obtain a specimen for each remaining specimen bottle.

DETAILED DESCRIPTION OF PREFERRED EMBODIMENTS

Figure 1:
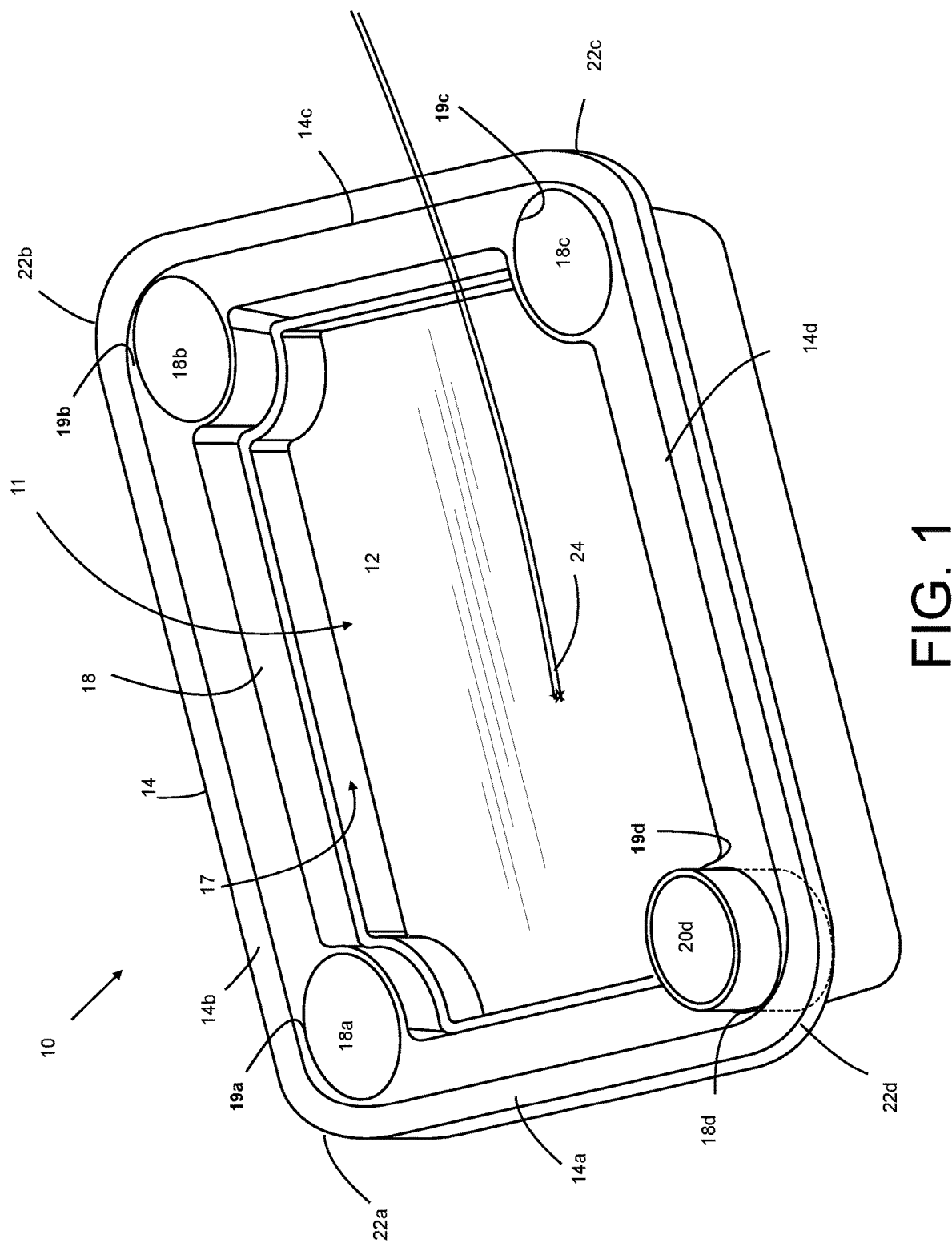
FIG. 1 illustrates a perspective view of one embodiment of a biopsy tray.
Figure 2:
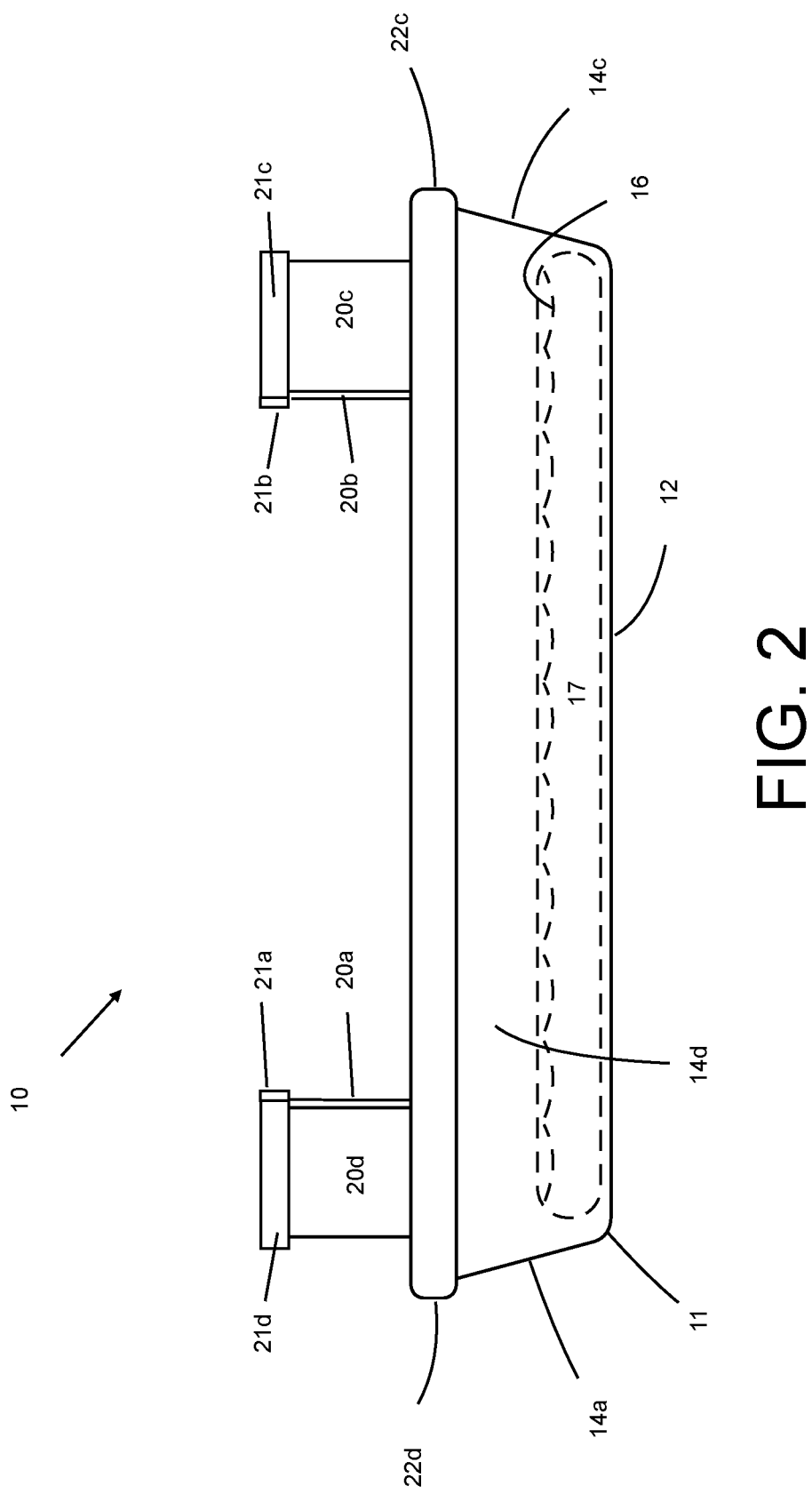
FIG. 2 illustrates a side view of the embodiment of a biopsy tray of the invention in FIG. 1.
Figure 3:
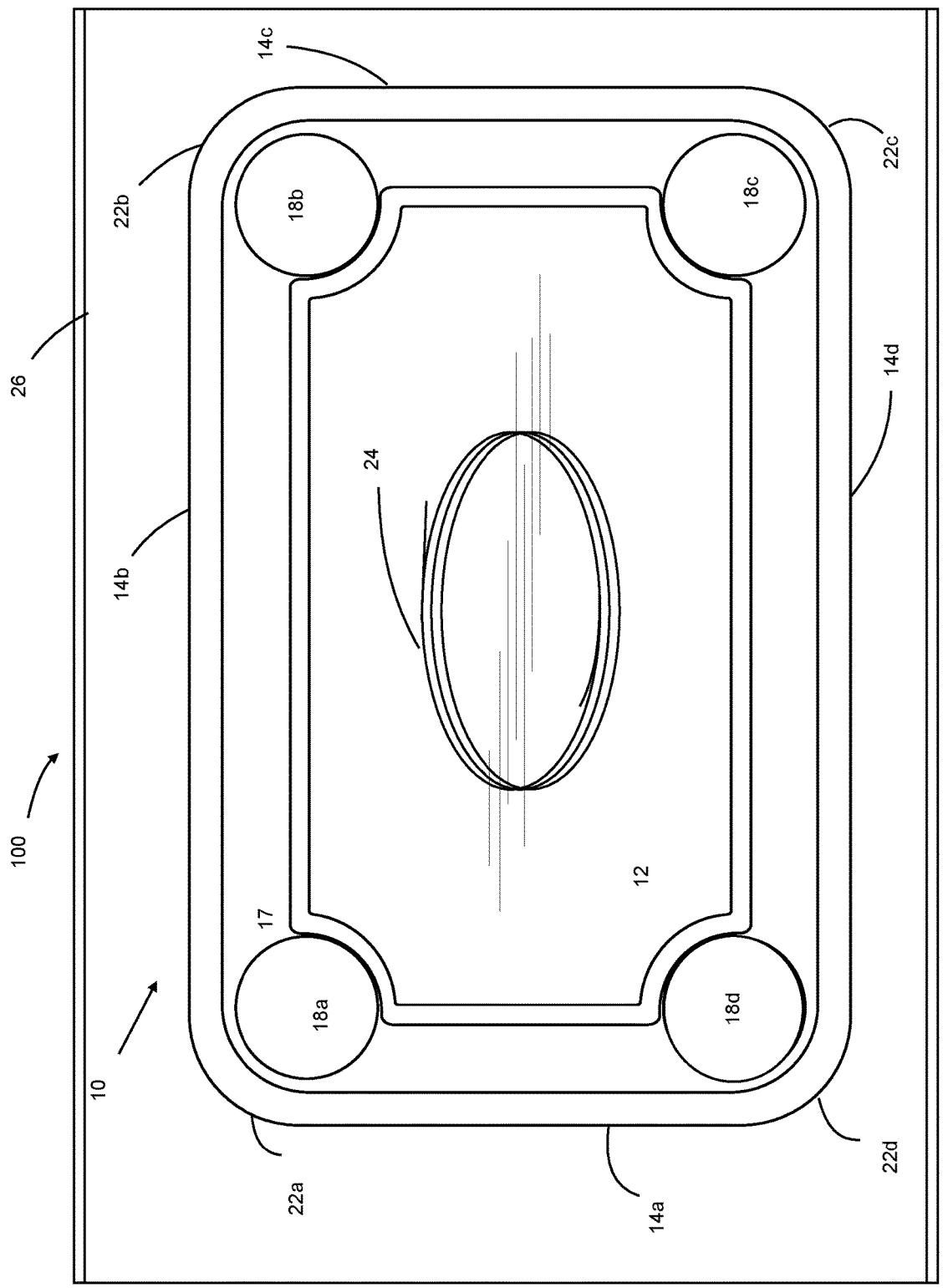
FIG. 3 illustrates a top view of the embodiment of a biopsy kit of the invention.

Referring now to the drawings, an improved biopsy tray and method of obtaining a biopsy specimen is provided. The embodiments are described with reference to the drawings and like elements are referred to by like numerals.

The relationship and functioning of the various elements of the embodiments are more fully understood by the following detailed description in viewing the drawings. The embodiments as described below are by way of example and the invention is not necessarily limited to the embodiments illustrated in the drawings. It should also be understood that the drawings are not to scale and in certain instances details have been omitted, which are not necessary for an understanding of the embodiments, such as conventional details of fabrication and assembly.

The improved biopsy tray is generally designated by the numeral 10. The biopsy tray 10 can preferably be made of a disposable sterile plastic, such as virgin BPA free polypropylene. The biopsy tray 10 includes container 11 having a bottom surface 12 and continuous perimeter wall 14, which here is shown to include four walls 14a, 14 b, 14c and 14d extending upward from the bottom surface 12 to form the container 11 and sufficient to hold an adequate amount of fluid 16 (cleaning liquid, e.g., 250 ml water) which is referred to hereinafter as a cleaning zone 17.

Figure 4:
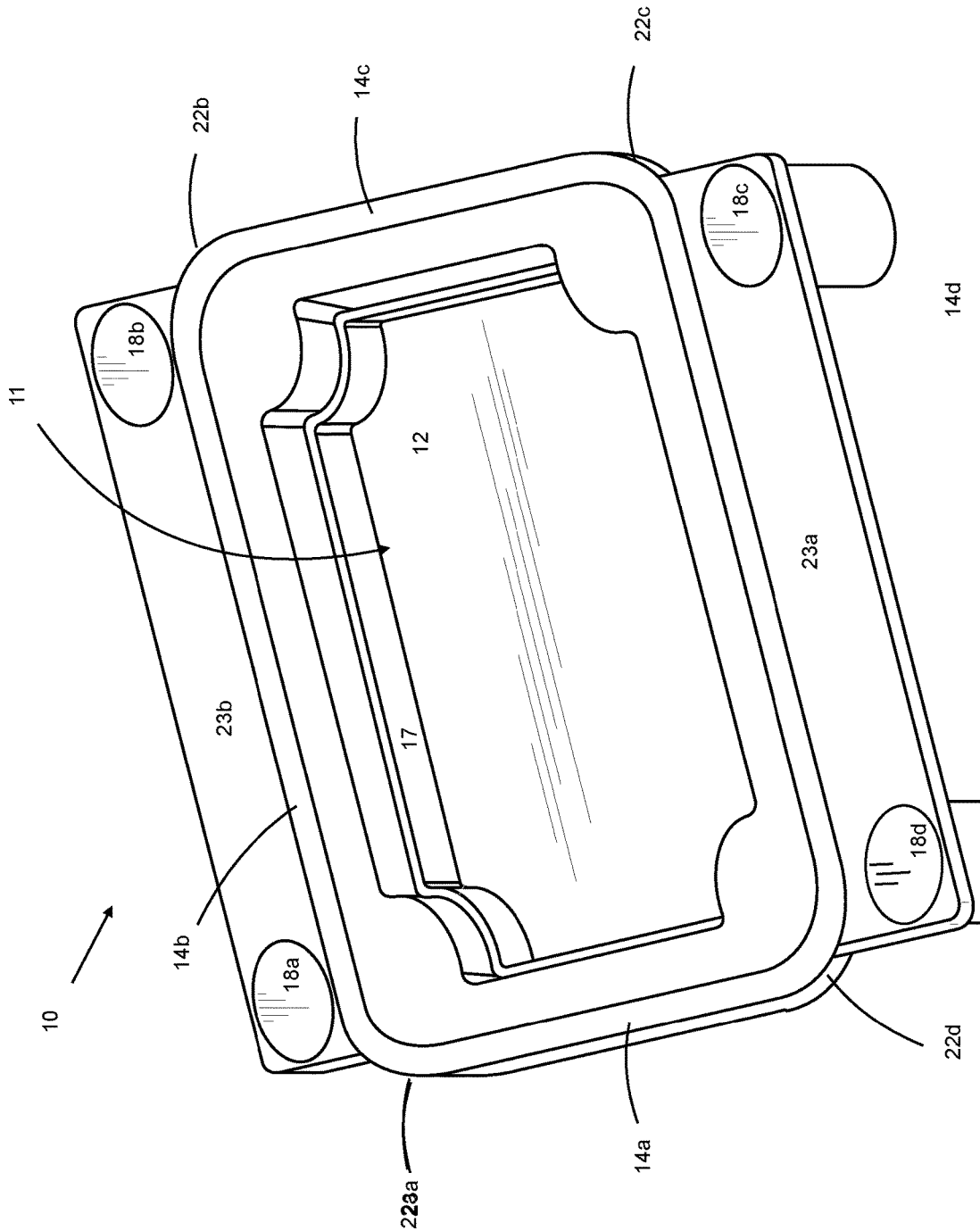
FIG. 4 illustrates a perspective view of another embodiment of a biopsy tray.
Figure 5:
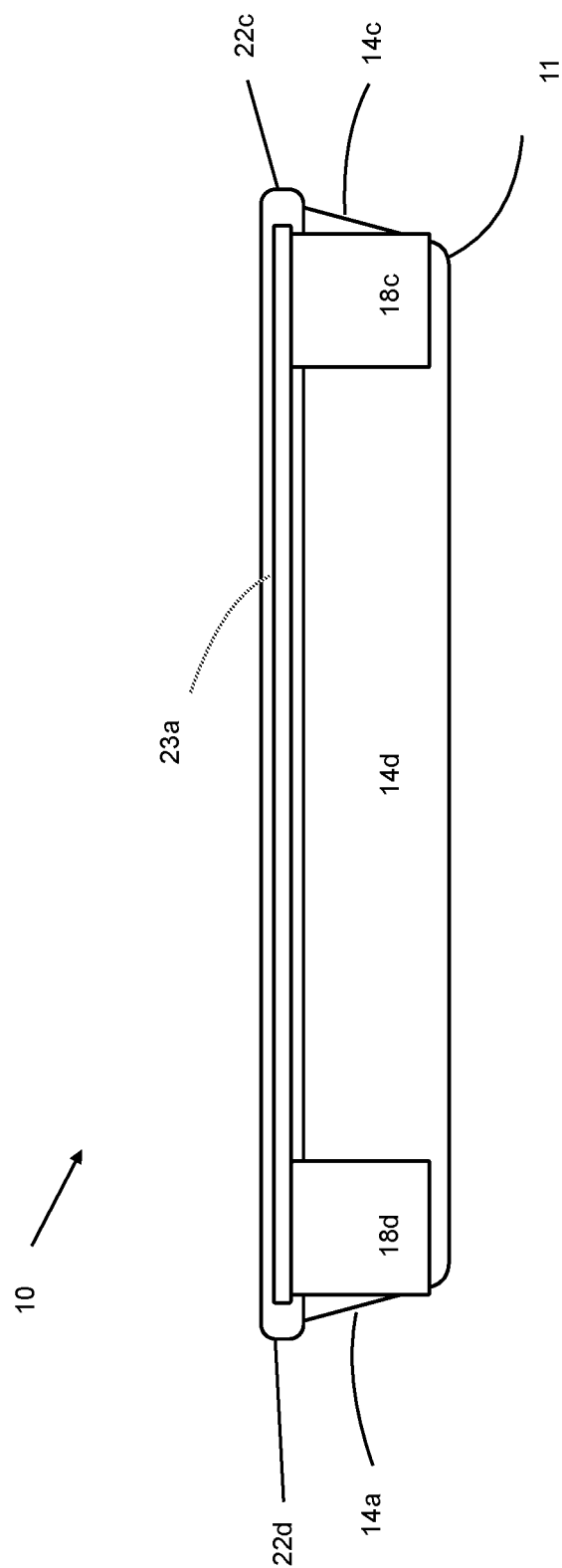
FIG. 5 illustrates a side view of the embodiment of a biopsy tray of the invention in FIG. 4.
Figure 6:
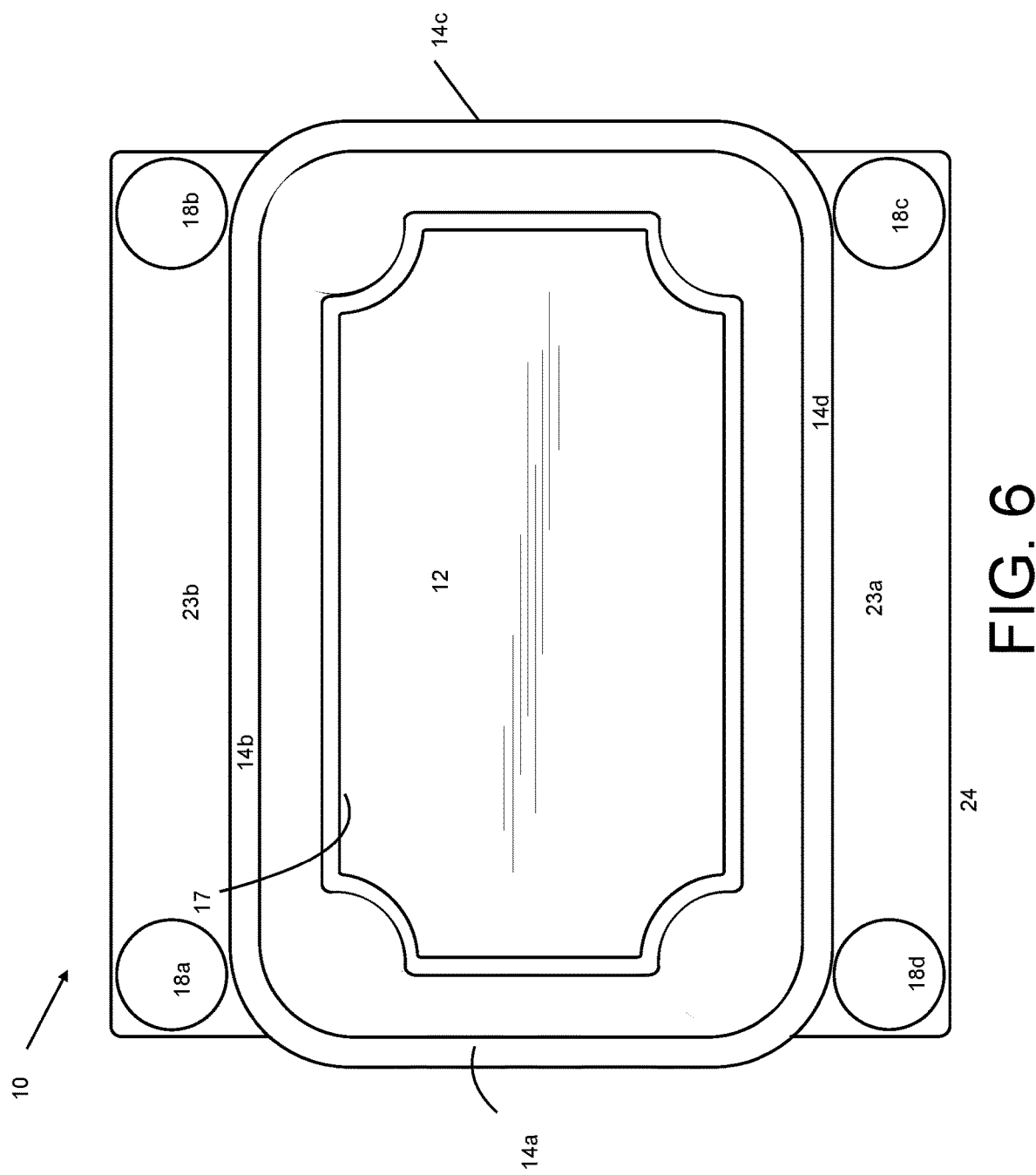
FIG. 6 illustrates a top view of the embodiment of a biopsy tray of the invention in FIG. 4.

Additionally the perimeter wall 14 includes at least one and preferably a plurality (e.g. four) of formed specimen bottle receiving receptacle surface(s) 18a, 18b, 18c and 18d and having a cylindrical opening(s) 19a, 19b, 19c and 19d which is above the bottom surface 12 in laterally outwardly spaced wall portion 18 separate from the cleaning zone 17 to receive and retain standard formalin specimen cylindrical bottles (e.g., 20 ml) 20a, 20b, 20c and 20d, respectively. While embodiment of the invention provides for the perimeter wall 14 to have four side walls 14a, 14 b, 14c and 14d with a formed bottle receiving receptacle 18a, 18b, 18c and 18d in a respective corner 22a, 22 b, 22c and 22d between each of the walls 14a, 14 b, 14c and 14d, it is contemplated that the formed bottle receiving receptacle surface 18a, 18b, 18c and 18d could be formed on another area of the tray 10, such as medially formed on each walls 14a, 14 b, 14c and 14d. Optionally, the formed bottle receiving receptacle surface 18a, 18b, 18c and 18d could be formed on outward extending panels 23a and 23b which extend from walls 14b and 14d, for example, as seen in FIGS. 4-6.

The specimen bottles 20a, 20b, 20c and 20d will be disposed in the bottle receiving receptacle surfaces 18a, 18b, 18c and 18d post water 16 or other cleaning solution being placed in the cleaning zone 17 of the tray 10. Preferably, the specimen bottle receiving receptacle surfaces 18a, 18b, 18c and 18d are formed as part of the tray 10 with opening(s) 19a, 19b, 19c and 19d above the bottom surface 12 and the tray cleaning zone 17 to isolate them from the cleaning zone 17. Once water is placed in the tray cleaning zone 17 and the specimen bottles 20a, 20b, 20c and 20d are inserted into the specimen bottle receiving receptacle surfaces 18a, 18b, 18c and 18d, caps 21a, 21b, 21c and 21d of the bottles 20a, 20b, 20c and 20d are removed and are ready to receive the specimen from forceps 24.

By so providing, it is not necessary that an attendant handle the specimen bottles 20a, 20b, 20c and 20d near the forceps 24 thus minimizing contamination or health risk. Preferably, the tray 10 is configured to at least partially nest on top of a like formed tray 10 thus providing for easy storage.

Another aspect of the invention is to provide a kit 100 which includes the above tray 10, biopsy forceps 24 and biopsy cover 26. The kit 100 is provided as a sterile set which is provided to perform a biopsy.

A method of obtaining a biopsy specimen is also provided. The method includes providing the tray 10 described above, filling the tray 10 with a sufficient amount of cleaning fluid, such as water 16, to enable cleaning of a biopsy forceps 24 post procedure. The method further includes placing one or more specimen bottle 20 in one or more bottle receiving specimen bottle receiving receptacle 18 and removing cap 21 from each one or more specimen bottle 20. The method includes employing a biopsy forceps 24 to remove a tissue specimen from a patient and placing the specimen into one of the specimen bottles 20 and removing the forceps 24 from the tray 10, then securing a cap 21 to the specimen bottle 20 and removing the specimen bottle 20 from the tray 10. The method further includes repeating the last step using the biopsy forceps 24 to obtain a specimen for each remaining specimen bottle 20.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the scope of the general inventive concept.

What is claimed is:

1. A kit for performing a biopsy, which includes:
   a biopsy tray which includes a container having a bottom surface and a continuous perimeter wall extending upward therefrom to form a cleaning zone which is sufficient to hold an adequate amount of fluid for cleaning a biopsy forceps, and at least one cylindrical specimen bottle receiving receptacle surface adjacent said perimeter wall and having a cylindrical opening which is above said bottom surface and said cleaning zone to receive and to retain a cylindrical specimen bottle and which is configured in a manner to extend outside said continuous perimeter wall which defines said cleaning zone laterally outwardly spaced thereto and in an isolated manner against fluid entry from said cleaning zone;
   a biopsy forceps; and
   a biopsy cover enclosing said tray and biopsy forceps.

2. A method of obtaining a biopsy specimen, which includes the steps of:
   a) providing a biopsy tray which includes a container having a bottom surface and continuous perimeter wall extending upward therefrom to form a cleaning zone which is sufficient to hold an adequate amount of fluid for cleaning a biopsy forceps, and at least one cylindrical specimen bottle receiving receptacle surface adjacent said continuous perimeter wall and having a cylindrical opening which is above said bottom surface and said cleaning zone to receive and to retain a cylindrical specimen bottle having a cap and wherein the at least one specimen bottle receiving receptacle surface is configured in a manner to extend outside said continuous perimeter wall which defines said cleaning zone laterally outwardly spaced thereto and in an isolated manner against fluid entry from said cleaning zone;
   b) filling said biopsy tray with a sufficient amount of cleaning fluid to enable cleaning said biopsy forceps post procedure;
   c) placing one of the one or more specimen bottles in said at least one or more specimen bottle receiving receptacle surface;
   d) removing the cap from each one or more specimen bottle;
   e) removing said forceps from the tray and employing the biopsy forceps to remove a tissue specimen from a patient and place the specimen into one of the one or more specimen bottles; and
   f) securing a cap to one of the one or more specimen bottles and removing the specimen bottle from the tray.

3. The method of claim 2, which further includes repeating the steps (e) and (f) to obtain a specimen for each remaining bottle.

* * * * *